US012629378B2

(12) United States Patent
Rossi et al.

(10) Patent No.: US 12,629,378 B2
(45) Date of Patent: May 19, 2026

(54) TREATMENT OF INFANTILE HEMANGIOMA

(71) Applicant: Arkayli Biopharma Inc., Madison, WI (US)

(72) Inventors: Thomas M. Rossi, Portsmouth, NH (US); Beth Drolet, Whitefish Bay, WI (US); Agis Kydonieus, Kendall Park, NJ (US)

(73) Assignee: ARKAYLI BIOPHARMA INC., Madison, WI (US)

( * ) Notice: Subject to any disclaimer, the term of this patent is extended or adjusted under 35 U.S.C. 154(b) by 1202 days.

(21) Appl. No.: 17/595,746

(22) PCT Filed: May 22, 2020

(86) PCT No.: PCT/US2020/034270
§ 371 (c)(1),
(2) Date: Nov. 23, 2021

(87) PCT Pub. No.: WO2020/242962
PCT Pub. Date: Dec. 3, 2020

(65) Prior Publication Data

US 2022/0218716 A1 Jul. 14, 2022

Related U.S. Application Data

(60) Provisional application No. 62/974,851, filed on Dec. 27, 2019, provisional application No. 62/921,007, filed on May 24, 2019.

(51) Int. Cl.

| | |
|---|---|
| ***A61K 31/5377*** | (2006.01) |
| ***A61K 9/00*** | (2006.01) |
| ***A61K 31/222*** | (2006.01) |
| ***A61K 47/10*** | (2017.01) |
| ***A61K 47/38*** | (2006.01) |
| ***A61P 17/00*** | (2006.01) |

(52) U.S. Cl.
CPC ........ *A61K 31/5377* (2013.01); *A61K 9/0014* (2013.01); *A61K 31/222* (2013.01); *A61K 47/10* (2013.01); *A61K 47/38* (2013.01); *A61P 17/00* (2018.01)

(58) Field of Classification Search
CPC ...... A61K 9/0014; A61K 47/10; A61K 47/38; A61K 31/222; A61K 31/215; A61P 17/00
See application file for complete search history.

(56) References Cited

U.S. PATENT DOCUMENTS

| | | | |
|---|---|---|---|
| 8,987,262 | B2 | 3/2015 | Leaute-Labreze et al. |
| 2013/0131181 | A1 | 5/2013 | Leaute-Labreze et al. |
| 2016/0184278 | A1 | 6/2016 | Bischoff et al. |
| 2018/0193320 | A1 | 7/2018 | Harton et al. |

FOREIGN PATENT DOCUMENTS

| | | | | | |
|---|---|---|---|---|---|
| CN | 103054793 | A | * | 4/2013 | |
| CN | 106176582 | A | * | 12/2016 | ........... A61K 31/165 |
| EP | 2050441 | A1 | | 4/2009 | |
| WO | WO-2008093356 | A1 | * | 8/2008 | ................ A61P 7/10 |
| WO | WO-2011039780 | A2 | * | 4/2011 | ............. A61P 31/04 |
| WO | 2018129364 | A1 | | 7/2018 | |

OTHER PUBLICATIONS

Bijaya et al., "Synthesis and evaluation of esmolol prodrugs for transdermal delivery", 2010, Drug Delivery, 17, pp. 532-540 (Year: 2010).*
Mehvar et al., "Stereospecific Pharmacokinetics and Pharmacodynamics of Beta-Adrenergic Blockers in Humans", 2001, J Pharm Pharmaceut Sci, 4, pp. 185-200 (Year: 2001).*
Extended European Search Report Application No. 20812951.0, dated May 24, 2023, 9 pages.
Fang et al., Determination of esmolol and metabolite enantiomers within human plasma using chiral column chromatography, Journal of Chromatography B, 878, 2010, 2449-2452, El Sevier.
PCT International Search Report and Written Opinion for International Application No. PCT/US2020/034270, dated Aug. 20, 2020, 5 pages.
McKee J.S et al., "An enantiomerically pure formulation of esmolol attenuates hypotension and preserves heart rate control in dogs," Anesthesiology, 2014, 121(6), pp. 1184-1193.
Tang L. et al., "Ultrasonication-assisted manufacture of cellulose nanocrystals esterified with acetic acid," Bioresour Technol, 2013, 127, pp. 100-105, biortech, Sep. 2012.
Rehman et al., "Atenolol," NCBI Bookshelf, StatPearls Publishing (2024) (available at https://www.ncbi.nlm.nih.gov/books/NBK539844/, last visited May 21, 2025), 10 pages.
Esmolol Hydrochloride Prescribing Information (2024) (available at https://www.accessdata.fda.gov/drugsatfda_docs/label/2024/205703s003lbl.pdf, last visited May 21, 2025), 17 pages.

* cited by examiner

*Primary Examiner* — Brenda L Coleman
*Assistant Examiner* — Madeline E Braun
(74) *Attorney, Agent, or Firm* — Hoffman Warnick LLC

(57) ABSTRACT

Transdermal delivery of beta blockers to treat Infantile Hemangiomas (IH) with reduced systemic circulation of the active drug and reduced or eliminated drug exposure to internal organs. In some embodiments, the beta blocker is esmolol. Pharmaceutical compositions according to the invention may be formulated lotions, creams, ointments, gels, foams, liquid dispersions, solutions, or aerosols.

15 Claims, No Drawings

TREATMENT OF INFANTILE HEMANGIOMA

CROSS-REFERENCE TO RELATED APPLICATIONS

This application claims the benefit of U.S. provisional applications 62/921,007 filed May 24, 2019 and 62/974,851 filed Dec. 27, 2019.

FIELD OF THE INVENTION

The invention pertains to the topical or transdermal delivery of beta blockers to treat Infantile Hemangiomas, deep, superficial, or mixed. In certain illustrative embodiments, the invention particularly pertains to beta blockers which have high permeability through skin, low penetration of the blood-brain barrier, and short half lives in vivo. In other embodiments, the invention pertains to beta blockers that are stereoisomers of a beta blocker that are substantially devoid of beta adrenergic receptor antagonist activity. The invention more particularly pertains to the topical or transdermal delivery of the beta blockers, Esmolol, and Landiolol, free bases or salts thereof, alone or in combination with one or more of chemical enhancers, esterase inhibitors, R-isomers of beta blockers and inert ingredients and with or without additional active pharmaceutical ingredients (APIs). The field of the invention further includes use of inactive stereoisomers, i.e., the R-isomers, of beta blockers to treat Infantile Hemangiomas, alone or in combination with or with one or more of chemical enhancers, esterase inhibitors, R-isomers of beta blockers and inert ingredients and with or without short half-life beta blockers or additional APIs.

BACKGROUND OF THE INVENTION

The invention pertains to more effective treatment of Infantile Hemangiomas (IH), using specific beta blockers administered topically/transdermally. IH are the most common tumor of childhood and are composed of proliferating endothelial-like cells. Approximately 80,000 infants annually are diagnosed with hemangiomas in the United States. The natural history of IH consists of rapid growth over the first year of life followed by involution over the next 5-10 years (N Engl J Med. 1999 Jul. 15; 341(3):173-181). The duration and rate of growth is variable; some infants will have hemangiomas that grow very little while others grow at an alarming rate. A Hemangioma Investigator Group (HIG) study identified low birth weight as the major risk factor for the development of IH, demonstrating a 25% increased risk of developing a hemangioma with every 500 gm reduction in birth weight. (J Pediatr. 2008 November; 153(5):712-715.e1).

Although many IH do not require intervention, 12-20% will have complications that require therapy. In a study of 1,058 infants with hemangiomas referred to seven academic centers in a period of 13 months, a 24% complication rate was observed, including ulceration (16.0%); threat to vision (5.6%); airway obstruction (1.4%); auditory canal obstruction (0.6%); and cardiac compromise (0.4%) (Pediatrics 2006 September; 118(3):882-887). These complications are the result of rapid growth requiring the early initiation of pharmacologic intervention, often in the first weeks of life. The indisputable indications for treatment are life- or function-threatening lesions (airway obstruction, vision loss, hearing loss, ulceration, and bleeding). More debatable indications are smaller facial lesions that may resolve over time but may leave permanent scarring and disfigurement.

Despite location or size, most parents seek some form of therapy in the hope of controlling growth or improving appearance. Agents with reported activity in treating IH include oral steroids, systemic interferon alpha, intravenous *vinca* alkaloids, and oral propranolol, oral nadolol, oral atenolol and topical timolol. Currently, there is only one drug, the oral agent propranolol, FDA-approved for the treatment of IH. There are no topical agents approved for this indication.

Beta blockers or beta adrenergic receptor blockers are a class of medications that are a principal treatment for cardiovascular disease including management of abnormal heart rhythms, ischemic heart disease, heart failure and hypertension. Beta blockers are competitive antagonists of epinephrine and norepinephrine on adrenergic receptors and can be beta one selective or nonselective. The beta one selective receptors are located mainly in the vasculature, heart and the kidneys. The primary antihypertensive mechanism of beta blockers as well as the mechanism for their effect on IH are unclear but may involve reduction in cardiac output due to negative chronotropic and inotropic effects and the release of renin by the kidney. R-isomers of beta blockers are not involved in the antihypertensive mechanism of beta blockers.

The following table lists some commonly known beta blockers, along with key information on their chemical structure, selectivity, elimination and dermal absorption properties.

| | Chemical Structure | Molecular Weight (D) | Melting Point (degrees C.) | LogP (L/H) | Skin Flux* ug/cm2/hr | Half-Life (hours) |
|---|---|---|---|---|---|---|
| Non--Selective Agents | | | | | | |
| Propranolol | 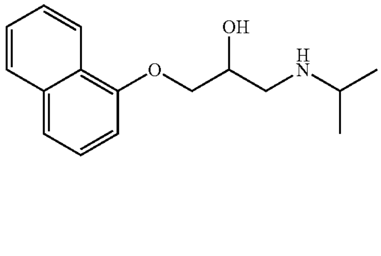 [SMILES: CC(C)NCC(O)COc1cccc2ccccc12] | 259.34 | 96 | 2.8 (L) | 70 | 4-5 |

-continued
| | Chemical Structure | Molecular Weight (D) | Melting Point (degrees C.) | LogP (L/H) | Skin Flux* ug/cm2/hr | Half-Life (hours) |
|---|---|---|---|---|---|---|
| Corteolol | 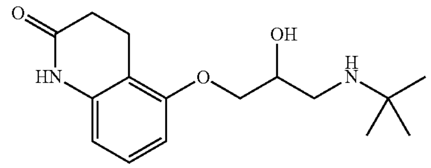 [SMILES: CC(C)(C)NCC(O)COc1cccc2c1CCC(=O)N2] | 292.373 | | | | 6-8 |
| Oxprenolol | 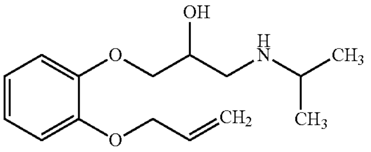 [SMILES: C=CCOc1ccccc1OCC(O)CNC(C)C] | 265.348 | | 2.1 (L) | 20 | 1-2 |
| Penbutolol | 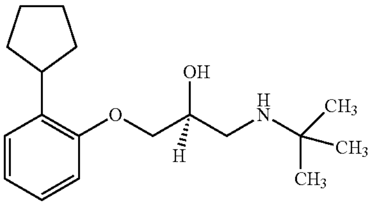 [SMILES: CC(C)(C)NC[C@H](O)COc1ccccc1C1CCCC1] | 291.428 | 171 | 4.15 (L) | | 20 |
| Pindolol | | 248.321 | | 1.75 (H) | 7 | 3-4 |
| Timolol | 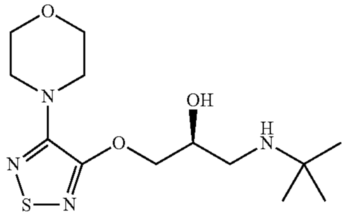 [SMILES: CC(C)(C)NC[C@H](O)COc1nsnc1N1CCOCC1] | 316.4 | | 1.4 (H) | 40 | 2.5-5 |
| Nadolol | 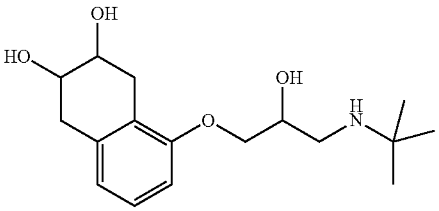 [SMILES: CC(C)(C)NCC(O)COc1cccc2c1CC(O)C(O)C2] | 309 | 124 | 1 (H) | 35 | 14-25 |
| Beta One Selective Agents | | | | | | |
| Atenolol | 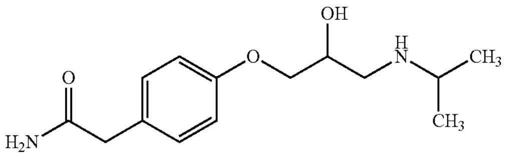 [SMILES: CC(C)NCC(O)COc1ccc(CC(N)=O)cc1] | 266.336 | 147 | 0.16 (H) | 9 | 6-7 |
| Metoprolol | 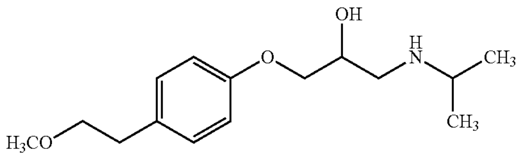 [SMILES: COCCc1ccc(OCC(O)CNC(C)C)cc1] | 267.369 | 120 | 1.88 (L) | 30 | 3-7 |

-continued

| | Chemical Structure | Molecular Weight (D) | Melting Point (degrees C.) | LogP (L/H) | Skin Flux* ug/cm2/hr | Half-Life (hours) |
| --- | --- | --- | --- | --- | --- | --- |
| Esmolol | 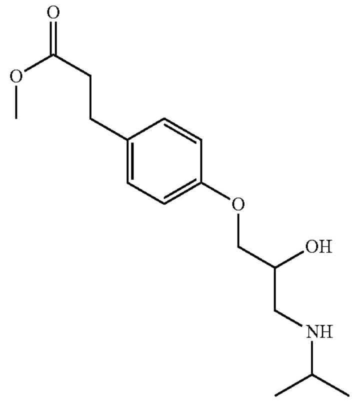 [SMILES: COC(=O)CCc1ccc(OCC(O)CNC(C)C)cc1] | 295.374 | 85 | 1.7 (H) | 70 | 0.15 |
| Landiolol | 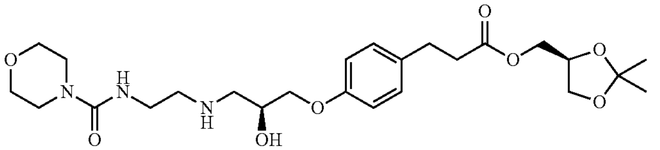 [SMILES: CC1(C)OC[C@@H](COC(=O)CCc2ccc(OC[C@@H](O)CNCCNC(=O)N3CCOCC3)cc2)O1] | 509 | 104 | 0.44 (H) | 0.2 | 0.05-0.1 |

*Estimated values

Ahad et al., Saudi Pharm. J. (2015) 23:587-602, reviewed papers describing systemic transdermal delivery of Propranolol (PP), Atenolol (AT), Metoprolol (MP), Bupranolol (BPL), Labetalol hydrochloride (LHCL), Carvedilol (CVD), Timolol maleate (TM) and Bisoprolol (BSP) and the effects of various chemical enhancers on skin permeation. Aqil, et al., Expert Opin. Drug Deliv. (2006) 3:405-418 provides an earlier such review.

Propranolol HCl, oral solution, was approved for the treatment of proliferating IH requiring systemic therapy in 1967. Püttgen et al., PEDIATRICS Volume 138, number 3, September 2016:e20160355, report a study of ophthalmic solution and gel-forming solution (GFS) formulations of timolol applied to the surface of hemangiomas in pediatric patients.

Bijaya, et al. (Drug Delivery, 2010 September-October, 17(7):532-540) have previously reported the use of propionate, butylate, and valerate prodrugs of Esmolol to increase skin flux by altering log P and melting point of the parent molecule. These prodrugs were then assessed for anti-hypertensive effect in animal models.

In summary, treatment options for IH include medical therapies (systemic, intralesional, and topical), surgery, and laser therapy. Propranolol has become the first-line oral medical therapy and off-label timolol maleate for topical delivery. Side effects of propranolol can include hypoglycemia (low blood sugar), bradycardia (low heart rate), hypotension (low blood pressure), sleep disturbance, and bronchospasm (wheezing/asthma). The most common serious adverse reaction is bronchospasm. Corticosteroids are rarely used due to their high rate of side effects such as immune suppression, hypertension, diabetes, and poor infant growth. Surgical excision of IH and laser surgery are rarely indicated and only used in special situations such as to treat painful ulceration of the hemangioma and cutaneous disorders which persist following involution.

Research to find other treatments with fewer side effects is ongoing. Work on oral beta blockers and renin-angiotensin inhibitors, is continuing. Oral mTOR inhibitors are also described as treatments for IH alone or in combination with oral beta blockers. Finally, several patent applications relating to compositions for the treatment of neoplastic and non-neoplastic hyperproliferative cell diseases describe their use for the treatment of IH.

SUMMARY OF THE INVENTION

The invention provides pharmaceutical compositions and methods that have surprising advantages over pharmaceutical compositions and methods previously described as useful in the treatment of IH.

In general terms, this invention resides in a pharmaceutical composition for the treatment of IH by topical application to the surface of an IH comprising an active pharmaceutical ingredient (API) or a pharmaceutically acceptable salt thereof and a pharmaceutically acceptable carrier wherein the API is a beta blocker that has a half-life in vivo, i.e., a plasma half-life, of less than one hour. In other embodiments, the API may be an inactive stereoisomer, i.e., the R-isomer, of a beta blocker or a combination of the beta blocker with a short half-life and the R-isomer of a beta blocker.

In some embodiments, the API is a beta blocker that has a half-life of less than one half hour such as Esmolol or Landiolol or pharmaceutically acceptable salts of Esmolol of Lendiolol. As used herein references to an API such as Esmolol or Landiolol include prodrugs such as esterified derivatives of the API.

In some embodiments, the invention comprises such pharmaceutical composition formulated as a lotion, cream, ointment, gel, foam, liquid dispersion or solution, or aerosol that is applied directly to the skin or is formulated for delivery in a reservoir type or polymeric matrix type transdermal patch or is formulated for delivery as an in situ patch.

In some embodiments, the invention comprises such pharmaceutical composition formulated with one or more of skin permeation enhancers and thickening agents.

In some embodiments, the API is the R-isomer of a beta blocker, which beta-blocker is active as a beta blocker in its racemic (i.e., a mixture of S and R isomers in any amounts but generally comprising >10% of more than one isomer) or resolved S-stereoisomer forms (i.e., generally ≥90% S isomer) but has little or no beta adrenergic antagonist activity in its resolved R-stereoisomer form.

In some embodiments of the composition of the invention, the API (a) is a beta blocker that has a half-life of less than one hour, (b) is the R-isomer of a beta blocker, or (c) is a combination of a beta blocker that has a half-life of less than one hour and the R-isomer of a beta blocker. Such compositions may, of course, also comprise additional APIs.

In further embodiments, the invention resides in a method of treating an Infantile Hemangioma by applying a pharmaceutical composition of the invention to the surface of the hemangioma.

DESCRIPTION OF THE INVENTION

The invention pertains to more effective treatment of IH, by delivering a novel agent topically/transdermally, directly into the targeted tissue of the skin, with much less active drug in systemic circulation, minimizing or eliminating drug exposure to the internal organs in which side effects are known to occur.

We have identified agents with a novel combination of properties suitable for topical treatment of IH. Considering the balance of these properties as they affect the suitability of each of certain beta blockers to enable the optimum topical treatment for infantile cutaneous hemangiomas, Esmolol (methyl 3-[4-[2-hydroxy-3-(propan-2-ylamino)propoxy]phenyl]propanoate) and Landiolol ([(4S)-2,2-dimethyl-1,3-dioxolan-4-yl]methyl 3-[4-[(2S)-2-hydroxy-3-[2-(morpholine-4-carbonylamino)ethylamino]propoxy]phenyl]propanoate) stand out as being particularly desirable. Esmolol alone has a combination of relatively high skin flux for local delivery of the drug into a cutaneous lesion plus very short half-life for rapid clearance after entering systemic circulation, and hence minimal systemic exposure and accumulation. Landiolol was developed by modifying the chemical structure of Esmolol. Although Landiolol has an estimated lower skin permeation rate than Esmolol, it has a 10-fold higher rate of cardiovascular (beta-1) selectivity, greater potency and shorter duration of action.

The rapid clearance of Esmolol and Landiolol derive from their metabolic properties. For example, once introduced to systemic circulation, Esmolol is taken up into the cytosol of red blood cells where carboxylesterases cleave the phenylpropionate moiety, releasing methanol and an inactive metabolite with 1/1500 the potency of Esmolol. This non-active metabolite is significantly more hydrophilic than Esmolol, and hence, will not partition significantly across the blood brain barrier. For the treatment of IH, this provides the additional advantage of minimizing the potential for CNS side effects and impairment of memory. Similarly, Landiolol is metabolized via hydrolysis of the ester moiety. It is rapidly hydrolyzed to an inactive form by both carboxylesterases in the liver and pseudocholinesterases in the plasma, resulting in a very short elimination half-life of about 4 minutes.

Commercially, Esmolol and Landiolol are available as intravenous products which are designed to be used in acute care settings. Cardiac response to beta blockers is variable. Therefore, the rapid elimination characteristics of the active moiety allow for nearly instantaneous discontinuation of therapy in the case of adverse reactions or overdosing. These agents are less likely to cause or exacerbate bronchospasm, the most common serious adverse event observed in children threatened with oral propranolol, and they can be used in infants and children with respiratory compromise or reactive airway disease. Due to the intravenous route of administration, the activity of carboxylesterases in the gut or other membranes is not problematic for presentation of the active moiety into systemic circulation.

However, in the present invention, the beta blocker must be delivered across the epidermis and into the dermis in order to reach the cutaneous hemangioma lesion. Given the metabolic lability of both Esmolol and Landiolol, the carboxylesterases contained in the skin present a problem that can be addressed in the current invention. This may be important for the co-delivery of other agents such as R-isomers which may have other side effects as well.

In the present invention, the beta blocker acts locally, i.e., at the site of the hemangioma. Therefore, as previously mentioned, the drug needs to penetrate into and preferably through the hemangioma and systemic delivery, i.e., delivery into the circulatory system, is not required. The present invention does not, however, exclude delivery through the skin and into the circulatory system, particularly in view of the relatively short half-lives of the beta blockers used in the present invention.

In this specification, the terms "topical" and "transdermal" both refer to delivery of an API to the surface of the skin and to delivery of drugs into the skin. They encompass both topical delivery in the form of, e.g., gels and creams applied directly to the skin as well as transdermal delivery in the form of patches. The patch systems can be classified in many ways, but they are mostly those that are called matrix patches where the active drug is incorporated in a polymer layer and those that are called reservoir patches where the drug is a solution, a gel, or a cream, enclosed between two or more polymer layers. In topical formulations as well as in reservoir type patch systems the gels or creams are formed by dissolving in the solutions small amounts of hydrophilic thickening polymers, such as hydroxypropyl cellulose (e.g., Klucel®), at, e.g., 0.1 to 5 wt. % or 0.1 to 1 wt. %. Both reservoir and matrix patch systems are well accepted with transdermal products of both types available in the marketplace. Transdermal delivery has been used with different drugs and it is well understood, (Transdermal Delivery of Drugs, Volumes I, II and III, CRC Press, 1987).

Chemical enhancers, i.e., skin permeation enhancers, can be used with both topical formulations (e.g., U.S. Pat. No. 9,186,352) as well as with patch formulations (e.g., U.S. Pat. No. 9,198,919). Common chemical enhancers include dimethyl sulfoxide (DMSO), ethyl alcohol, lauryl lactate, ethyl lactate, capric acid, oleic acid, oleyl alcohol, glycerol monooleate, levulinic acid, propylene glycol, polyethylene glycol, diethylene glycol monoethyl ether, and dipropylene glycol among others. In an illustrative embodiment, the enhancer comprises 10-25% (preferably 15-20%) propylene glycol, 10-25% (preferably 15-20%) polyethylene glycol, e.g., PEG 400, 10-25% (preferably 15-20%) DMSO, 5-20% (preferably 5-15%) diethylene glycol monoethyl ether, e.g., Transcutol® P, and 1-10% (preferably 2-6%) oleyl alcohol, with all percentages being wt. %. The book Percutaneous Penetration Enhancers, CRC Press, 1995, describes dozens of chemical families that can be used as enhancers and over 100 individual chemicals.

The main component of the active portion of the patch is the pressure sensitive adhesive (PSA) into which the drug is dissolved or dispersed. Commercially used PSA adhesives include acrylic polymers and copolymers, silicones and polyisobutylenes and they represent anywhere from 50 to 95% of the drug active matrix. Acrylate PSAs have great flexibility because of their ease in forming copolymers and allowing larger amounts of drugs to be incorporated within (e.g., U.S. Pat. No. 9,539,201). Because they are more hydrophilic than other PSAs, they are not commonly used for adhesion to skin for more than three and one half days. Polyisobutylene adhesives are the most hydrophobic and they are often used for the development of patches that adhere to the skin for seven days. These PSAs are however not easy to modify, so in many cases the active portion of the patch, where the drug is dissolved, is made of acrylate adhesive and there is a peripheral adhesive attached to the back side of the patch and extending in all direction beyond the active patch to provide for long term adhesion of over seven days (U.S. Pat. No. 8,246,978).

The pharmaceutical composition of the invention optionally also comprises excipients such as gelling agents, plasticizers, humectants, buffers, and the like. The composition can be formulated and applied to the skin, for instance, as a lotion, cream, ointment, gel, foam, liquid dispersion or solution, or aerosol that can be applied directly to the skin, or it can be contained within a transdermal delivery device, such as a patch, in which the composition is contained, for example, within a reservoir by a semi-permeable membrane or as a soft polymeric matrix such as a pressure sensitive adhesive that is in direct contact with the skin, i.e., that is firm enough that a permeable membrane is not required.

Humectants can be used in transdermal patches to absorb the transepidermal water loss and reduce irritation. Humectants are water soluble or swellable polymers and those more commonly used include polyvinyl pyrrolidone and polyvinyl pyrrolidone/vinyl acetate copolymers (e.g., U.S. Pat. Nos. 9,050,348; 9,539,201). Such humectants can also function as plasticizers.

Antioxidants can also be used in the active portion of the patch if the drug is susceptible to oxidation. Oxidation can take place from oxygen permeating through the packaging film or from the inactive ingredients in the patch. For example, acrylate pressure sensitive adhesives as well as polyvinyl pyrrolidone are manufactured by free radical polymerization processes. Therefore, free radicals remaining within these polymers may degrade a susceptible drug when incorporated into these polymers (e.g., U.S. Pat. No. 9,364,487). Useful antioxidants include sodium bisulfite, sodium sulfite, isopropyl gallate, Vitamin C, Vitamin E, butylated hydroxyanisole (BHA), butylated hydroxytoluene (BHT), pentaerythritol tetrakis(3-(3,5-di-tert-butyl-4-hydroxyphenyl) propionate), or tris (2,4-di-tert-butylphenyl) phosphite.

Esterase inhibitors can be used with topical or transdermal delivery systems to protect the drug from metabolizing to a non-active metabolite during its passage through the skin. Quinones, diones, isatins, flavanoids, fatty acids, sterols, myristic acid, sodium benzyl sulfate, and castor oil are some esterase inhibitors among many others that can be used (Current Medicinal Chemistry, 2018, Vol. 25, No. 14, p 1627).

The formulation of the invention can also comprise one or more preservatives, e.g., benzododecinium bromide 0.012%.

Oral propranolol has become the first line therapy for babies with complicated IH. The drug is effective and has been rapidly adopted, transforming care for infants with these vascular tumors. Although propranolol has been well studied in adults, observations of its use in infants and children, nearly 40 years in duration, have been mainly anecdotal. Based on case reports and case series, oral propranolol appears to have a favorable safety profile in children. Deaths or acute heart failure have very rarely been associated with propranolol use for IH. As a β-blocker, propranolol decreases heart rate and, in part, blood pressure as a result of negative chronotropic and inotropic effects on the heart. Propranolol's effect on blood pressure and heart rate in children peaks around 2 hours after an oral dose. It is therefore one embodiment of our invention to use a beta blocker with a very short half-life to eliminate or minimize the cardiovascular side effects presented by the only FDA-approved agent, the non-selective beta blocker, propranolol.

Most adverse events from oral propranolol are related to its non-cardio-selective nature. Severe hypoglycemia and hypoglycemic seizures have been reported in infants with IH treated with oral propranolol. These cases occurred in both newborns and toddlers and were often associated with poor oral intake or concomitant infection. This is caused by the beta two inhibition of gluconeogenesis which is a critical pathway in regulating glucose metabolism in infants. Likewise, bronchial hyperactivity, described as wheezing, bronchospasm, or exacerbation of asthma/bronchitis, is a recognized side effect of propranolol as the result of its direct effect on beta two adrenergic receptors on bronchioles of the lung.

Unfortunately, there are limited available data on long-term effects of extended use of oral propranolol during infancy. Given the pharmacologic properties and the lipophilic nature of propranolol there is growing concern about the long-term neurocognitive impact of propranolol use in infants and children treated for IH during the most susceptible developmental period. A recent review suggested that in adults oral propranolol interferes with neural pathways critical for higher level brain function such as learning and memory, which could be an unrecognized long-term side effect of its use (Lonergan et al., J Psychiatry Neurosci. 2013 July; 38(4)). However, as these higher level skills cannot be reliably assessed until children are 6 years old, there is a potential that critical adverse effects may go undetected or will not get attributed to the agent used during infancy. Propranolol penetrates the blood brain barrier and blocks the effects of norepinephrine. Norepinephrine enhances learning and memory formation. Long-term blockade of norepinephrine in the brain, particularly in infants during their early developmental stages, may impair learning and memory formation. The exact magnitude of CNS effects resulting from propranolol use, especially in the early developmental stages and for prolonged periods of use, is not known. These effects may not be readily recognizable and require specialized assessment of cognitive function. Furthermore, there may be a delay between exposure and manifestation of cognitive defects. Clinicians are now using this drug as well as topical beta blockers for small, non-complicated hemangiomas. Given the likelihood for increased exposure and limited existing long-term safety data, this represents an urgent public health need. It is therefore another embodiment of our invention to use beta one selective blocker which has favorable physical chemical properties to penetrate the skin, but which is rapidly metabolized to a more hydrophilic form which does not significantly penetrate the blood-brain barrier to minimize the interference of neural pathways and sleep disturbance and presented by the only FDA-approved agent, the non-selective beta blocker propranolol.

In summary, our invention comprises: a) topical delivery of a beta blocker to minimize the systemic effects of the beta blocker—the administration of the beta blocker can be delivered topically using, e.g. sprays, solutions dispersions, gels, creams, foams, or patches; b) a beta blocker with very low plasma half-life, i.e., less than 1 hour, preferably less than 0.5 hour and more preferably less than 15 or even 10 minutes, which can minimize the potential of the beta blocker to cause side effects in other organ systems. In illustrative embodiments, the beta blocker has one or more of the following properties: it is metabolized to a hydrophilic form that will not significantly penetrate the blood-brain barrier, it is highly selective for the beta-1 adrenoceptor, e.g., at least 25 times greater affinity for the beta-1 receptor than for the beta-2 receptor.

In an illustrative embodiment, the invention comprises transdermal co-delivery of R-isomers of any beta blocker.

The success of oral propranolol for IH treatment has led many practitioners to use topical beta blockers off-label for the treatment of smaller hemangiomas. In the U.S. there are no commercially available forms of propranolol designed for application to the skin; however, intraocular preparations of timolol are FDA approved to treat children with glaucoma. Publications on the use of timolol maleate ophthalmologic solution or gel-forming solution applied directly to hemangiomas on the skin or mucosa for off-label use in IH are rapidly emerging. None of these preparations are approved for the treatment of IH. Ophthalmic preparations of beta blockers such as 0.1% or 0.5% timolol maleate gel-forming solutions have been applied to the skin with promising results. See, e.g., Püttgen et al, PEDIATRICS Volume 138, number 3, September 2016:e20160355. Clinicians frequently turn to topical beta blockers for treatment of small, non-complicated IH with the presumption that topical application will result in less systemic drug exposure and an improved safety profile when compared to oral administration of beta blockers. Given the perceived safety with topical application, many infants who previously did not receive therapeutic intervention may now be prescribed topical timolol ophthalmic preparations. These preparations were exclusively designed to be administered as intra-ocular inoculation (eye drops) and viscosity of the gels designed to minimize draining into the nasal mucosa through the tear ducts. These products were not intended to be applied to the skin and pharmacokinetics for use on the skin to treat IH are just now being investigated. Timolol has been found to be 4-10 times more potent when compared with propranolol, and systemic absorption has been reported with both of the intraocular application of timolol mentioned above. A study conducted in 2002 demonstrated that approximately 80% of each drop (0.05 mL) of timolol 0.5% solution administered to the eye of an adult was systemically absorbed through the ocular mucosa. Systemic adverse effects such as bradycardia, hypoglycemia, and bronchial hyperreactivity were observed in 3-4% of children with pediatric glaucoma when treated with intraocular timolol. Preliminary data from the first population pharmacokinetic analysis of timolol ophthalmic preparations being applied to the skin over IH has demonstrated significant transcutaneous absorption of timolol. Timolol was detected in 93% (86/92) of the plasma samples tested. Concentrations were highly variable, with 80%>0.2 ng/mL, the plasma concentration demonstrated to have measurable systemic beta-blocking activity in adults. The plasma levels were highly variable with mean 7.1±18.2 ng/ml (median 0.98 ng/mL [0.03-106]), even when normalized for dose (mean 24.1±62.7 ng/ml/mg, median 3 ng/ml/mg [0.06-424]). 12/86 samples were between 0.020-0.2 ng/mL. Eighty percent of samples had plasma levels >0.2 ng/mL, the plasma level demonstrated to have beta blocking activity in adults. Ten subjects had plasma levels ≥10 ng/mL, similar to what is observed with intravenous administration. These levels appear to be higher than those observed in children with glaucoma receiving intra-ocular inoculation of timolol (Drolet et al., Pediatric Trials Network Steering Committee. Systemic Timolol Exposure Following Topical Application to Infantile Hemangiomas. J Am Acad Dermatology 2020).

Given the systemic drug exposure with off-label use of topical timolol for IH, it is yet another embodiment of our invention to use a beta blocker which metabolizes rapidly after its permeation through the skin so there is no or minimal b-adrenergic antagonism when the metabolite reaches the systemic circulation and co-delivery with other excipients such as R-Isomers of beta blockers that are not able to cause beta blockade. It is still another embodiment of our invention to use the beta blocker Esmolol or Landiolol for the treatment of IH using topical/transdermal administration. Esmolol and Landiolol are beta one selective beta blockers which have reasonable unenhanced skin permeation, which permeation can be increased by the use of safe enhancing systems or decreased by dropping the Esmolol or Landiolol degree to saturation in the formulation to the desired level. Enhancing transdermal delivery of Esmolol and Landiolol and administering it directly to the IH, will allow for higher target tissue drug concentrations of beta blockers and decreased systemic exposure, when compared to oral or parenteral beta blocker administration. In addition, it is another embodiment of our invention that these drugs will be delivered transdermally over an extended period of time, thereby providing higher target tissue concentrations for a sustained period of time. This is a distinct advantage over the FDA-approved twice daily orally administered propranolol, in which there are known to be large variations in plasma peak to trough levels.

Esmolol and Landiolol are cardioselective beta one receptor blockers with rapid onset, a very short duration of action, and no significant intrinsic sympathomimetic or membrane stabilizing activity at therapeutic dosages. They are delivered intravenously from solutions with very low concentrations, e.g., 1 mg per mL. They have rapid distribution half-life of about 2 minutes and an elimination half-life of less than 9 minutes. They are rapidly metabolized by hydrolysis of the ester linkage, chiefly by the esterases in the cytosol of red blood cells and not by plasma cholinesterases or red cell membrane acetylcholinesterases to free acid metabolites. The metabolism of Esmolol and Landiolol by the esterases in the skin can be modulated by the concomitant use of esterase inhibitors or competitors. There is a large number of esterase inhibitors, e.g., quinones, isatins fatty acids or esters, flavonoids, sterols, myristic acid, castor oil, and mixtures thereof. The esterase inhibitors can also be used to pretreat the skin, just before the topical application of the formulation containing Esmolol or Landiolol. It is yet another object of our invention to pretreat the skin or incorporate into the topical formulations, esterase or cholinesterase inhibitors, to prevent metabolism of the drugs as they transit through the epidermis.

Esmolol, like other beta blockers listed in the above table, are commercialized as racemic mixtures. For example, the beta one receptor blocking activity of Esmolol is due to its levo rotatory isomer, i.e., the S-isomer. It is yet another object of the invention to utilize the appropriate rotary isomer of the beta blocker, in preference to the racemate. This effectively halves the amount of drug that must be delivered across the skin in a given period of time in order to reach a therapeutically effective level within the lesion.

In another aspect of this invention, the chemical structure of Esmolol and Landiolol are modified by varying the blocking groups around the ester moiety. For example, the structure of Esmolol is modified by varying the number of methyl groups in the propionate side chain. This does not alter the beta one selectivity (which is known to be derived from the para position of the side chain) but does alter the rate of carboxylesterase activity through steric hindrance of the enzyme activity. Although this increases the circulating half-life of the Esmolol derivative, it also decreases the extent of xenobiotic deactivation in the skin prior to reaching the lesion, thus allowing a fine tuning of the balance of delivery and elimination rate.

In yet another embodiment of this invention, the free hydroxyl group on the phenoxy propanolamine scaffold is esterified with, e.g., a C1-C10 carboxyalkyl to form an alkyl ester including but not limited to formate, acetate, propionate, butyrate (e.g., tert-butyrate), valerate. It is thought that such ester side chains can aid in the delivery of a beta blocker across the stratum corneum. Such ester derivatives of Esmolol and Landiolol are preferred. Without intending to be bound to a particular mechanism, it appears that the ester side chains improve the log P and melting point and also provide a competitive site for carboxylesterase activity and rapid conversion to Esmolol or Landiolol; once bound to caroboxylesterase 1 (CE1) or caroboxylesterase 2 (CE2) in the skin, the ester derivatives are sterically inhibited from interacting with a second carboxylesterase enzyme, thus preserving the active moiety as it transits through the skin. Such esters are typically unsubstituted but substitution with groups that do not adversely affect the properties of the molecule can be used.

The invention may comprise combination therapies in which a patient is treated by transdermal delivery of a beta blocker having a short half-life and sequentially or concomitantly with another method of treatment. Such other method can be, e.g., intravenous or oral administration of a beta blocker having a longer half-life or that is less cardioselective, For example, the invention may comprise co-treatment with low dose oral propranolol, e.g., 50% or less of the US FDA-approved dose. As previously mentioned, the invention may also comprise coadministration with the resolved R isomer of any beta blocker including e.g., a beta blocker that has a longer half-life. In this specification and claims, by "resolved" is meant that the beta blocker or R isomer of a beta blocker is substantially free of other stereoisomers, e.g., at least about 90% pure relative to other stereoisomers, preferably at least about 95% pure and more preferably at least about 99% pure. Other treatment methods that do not comprise beta blockers can also be used in combination with a beta blocker as described herein, e.g., corticosteroids or inhibitors of platelet-derived growth factor (PDGF), e.g., itraconazole, to promote involution or of PDGF, e.g., becaplermin, to enhance healing of ulceration. The method of the invention can also be carried out as an adjunct to surgical removal of a hemangioma.

Examples

Example 1. Solubility of Esmolol in Various Solvents.

Knowing the solubility of a drug in different excipients and chemical enhancers is important in optimizing the saturation solubility of the drug in topical and transdermal formulations. Here below is a table (Table 1) showing the solubility of esmolol in several excipients and chemical enhancers. The solubility of Esmolol was higher in hydrophilic excipients and lower in the more lipophilic excipients. Several of these compounds were used to prepare the formulations in Example 2, such as the co-enhancing system of oleyl alcohol and propylene glycol.

TABLE 1

Esmolol Solubility in Various Excipients

| Solvent | Sat. Conc. (mg/mL) |
|---|---|
| Propylene Glycol | 450.7 |
| PEG-400 | 248.6 |
| DMSO | 592.1 |
| Dipropylene Glycol | 257.6 |
| Oleyl Alcohol | 112.2 |
| Transcutol P | 344.5 |
| Ethanol | 310.4 |
| Water | 704.1 |
| Isopropyl myristate (IPM) | 196.2 |
| Castor Oil (CO) | 23.4 |
| Cotton seed oil (CSO) | 101.9 |
| Olive Oil (OO) | 58.1 |
| Sesame oil (SO) | 56.6 |
| Glyceryl monooleate (GMO) | 157.3 |
| Lauroglycol FCC (LG) | 122.2 |
| Oleic acid (OA) | 56.9 |

Example 2. In Vitro Enhanced Skin Permeation of Esmolol.

One skin donor and three diffusion cells per formulation were used in these in vitro skin permeation experiments. Split thickness dermatomed (approximately at 375 μm) human cadaver skin was used to determine the permeation rate of the beta blocker Esmolol in vitro. All in vitro skin permeation studies were conducted using the PermeGear Membrane Transport System. Each Membrane Transport System consists of vertical, jacketed (37° C.±0.5° C.) Franz diffusion cells with magnetic stirrer and 1.7 $cm^2$ diffusion area.

Skin flux studies were run for a period of 24 hours. At predetermined intervals after starting the experiment, the entire contents of the receiver compartment were collected for determination of the Esmolol concentration by HPLC. The receiver compartment was refilled with fresh receiver medium. The receiver medium was pH 7.4 water with 0.44 mg/ml of Oleath 20 with the saturation concentration of the drug in the receptor medium being 0.5 mg/ml or about 6 mg total in the receptor phase. This solubility of the drug in the receiver medium was sufficient to ensure sink conditions throughout each collection interval. The donor phase was composed of a saturated gel solution of Esmolol in different solvents and enhancers. Three gel formulations were prepared as shown in Table 2 and used as the donor phase.

In addition, two formulations of Timolol were used as controls. The Timolol ophthalmic solution and the Timolol ophthalmic gel forming solution (GFS). Both of these are commercial products and were used in the treatment of IH with some success. No modifications to these formulations were made and they were used directly as dispensed from the commercial products.

The cumulative average permeation values in micrograms per square centimeter per hour calculated for the three Esmolol formulations (ES-1, ES-2, ES-3) and the two timolol commercial products are shown in Table 3.

From the data it can be seen that skin permeation is substantially higher with all three of the Esmolol formulations than that of either of the two commercial timolol products. The Esmolol skin permeation can of course be modulated, if needed, by reducing the enhancers used and also by reducing the Esmolol degree to saturation in the gel formulation.

TABLE 2

Esmolol Gel Formulations

| | ES-1 (%) | ES-2 (%) | ES-3 (%) |
|---|---|---|---|
| Propylene Glycol | 57 | 78 | 16 |
| Polyethylene Glycol (PEG 400) | — | — | 16 |
| DMSO | — | — | 16 |
| Transcutol ® P (diethylene glycol monoethyl ether) | — | — | 12 |
| Oleyl Alcohol | — | — | 4 |
| Esmolol | 43 | 22 | 36 |
| Hydroxypropyl cellulose (HPC) | 0.2 | 0.2 | 0.2 |
| Total | 100 | 100 | 100 |

TABLE 3

Cumulative average skin permeation of three esmolol gels and two timolol commercial products (micrograms/$cm^2$)

| hr | ES-1 | ES-2 | ES-3 | Timolol ophthalmic solution | Timolol ophthalmic GFS |
|---|---|---|---|---|---|
| 2 | 43.7 | 0.0 | 30.4 | 13.3 | 1.0 |
| 4 | 37.5 | 57.8 | 237.8 | 22.3 | 5.7 |
| 8 | 162.8 | 226.0 | 873.8 | 127.1 | 17.8 |
| 24 | 739.2 | 1015.9 | 3464.5 | 464.8 | 148.2 |

Example 3. Skin Permeation of Esmolol from Gels with and without an Esterase Inhibitor.

One skin donor and three diffusion cells per formulation are used in these in vitro skin permeation experiments. The experiment was performed using the same instruments and methodologies as described in Example 2. Two formulations are used: C, which is the same as ES-1, and D, which is the same as ES-1 but modified by addition of 1% each of the esterase inhibitors myristic acid and castor oil. The skin permeation experiment is performed for 24 hours and the flux is obtained in micrograms per $cm^2$ per hour for the two formulations.

Example 4. Skin Permeation of Landiolol from Gels with Enhancers and Esterase Inhibitors.

One skin donor and three diffusion cells per formulation are used in these in vitro skin permeation experiments. The experiment is performed using the same instruments and methodologies as described in Example 2. Formulation E is a gel and contains the esterase inhibitor myristic acid and the chemical enhancer ethyl alcohol. Formulation F is also a gel containing the cholinesterase inhibitor galanthamine hydrobromide and the chemical enhancer is decylmethylsulfoxide. The skin permeation experiment is performed for 24 hours and the flux is obtained in micrograms per $cm^2$ per hour for the two formulations.

While this invention has been described in conjunction with the specific embodiments outlined above, alternatives, modifications and variations will be apparent to those skilled in the art and in any case are intended to be embraced within the scope of this invention. Accordingly, the embodiments of the invention as set forth above are intended to be illustrative, not limiting. Various changes may be made without departing from the spirit and scope of the invention as defined in the following claims. All patents, patent applications, scientific articles, and other published documents cited herein are hereby incorporated by reference in their entirety for the substance of their disclosures.

What we claim is:

1. A pharmaceutical composition comprising:

esmolol or a pharmaceutically acceptable salt thereof in an amount effective to treat an Infantile Hemangioma (IH) by topical application to a surface of the IH;

a skin permeation enhancer; and a pharmaceutically acceptable carrier.

2. The pharmaceutical composition of claim 1 that is formulated as a lotion, cream, ointment, gel, foam, liquid dispersion or solution, or aerosol that is applied directly to the skin, is formulated for delivery in a reservoir type or polymeric matrix type transdermal patch, or is formulated for delivery as an in situ patch.

3. The pharmaceutical composition of claim 1 wherein the skin permeation enhancer is selected from the group consisting of: propylene glycol, polyethylene glycol, DMSO, diethylene glycol monoethyl ether, and oleyl alcohol.

4. The pharmaceutical composition of claim 1, further comprising hydroxypropyl cellulose.

5. The pharmaceutical composition of claim 1, formulated as a lotion.

6. The pharmaceutical composition of claim 1, formulated as a cream.

7. The pharmaceutical composition of claim 1, formulated as an ointment.

8. The pharmaceutical composition of claim 1, formulated as a gel.

9. The pharmaceutical composition of claim 1, formulated as a solution.

10. A method of treating an Infantile Hemangioma that comprises applying to a surface of the Infantile Hemangioma a therapeutically effective amount of the pharmaceutical composition of claim 1.

11. A method of treating an Infantile Hemangioma that comprises applying to a surface of the Infantile Hemangioma a therapeutically effective amount of the pharmaceutical composition of claim 5.

12. A method of treating an Infantile Hemangioma that comprises applying to a surface of the Infantile Hemangioma a therapeutically effective amount of the pharmaceutical composition of claim 6.

13. A method of treating an Infantile Hemangioma that comprises applying to a surface of the Infantile Hemangioma a therapeutically effective amount of the pharmaceutical composition of claim 7.

14. A method of treating an Infantile Hemangioma that comprises applying to a surface of the Infantile Hemangioma a therapeutically effective amount of the pharmaceutical composition of claim 8.

15. A method of treating an Infantile Hemangioma that comprises applying to a surface of the Infantile Hemangioma a therapeutically effective amount of the pharmaceutical composition of claim 9.

* * * * *